United States Patent [19]

Reierson

[11] 4,127,497
[45] Nov. 28, 1978

[54] MICHAEL ADDUCTS OF (SUBSTITUTED) CYCLOPENTADIENE AND ESTERS: A PROCESS THEREFOR AND DERIVATIVES THEREOF

[75] Inventor: Robert L. Reierson, Midland, Mich.

[73] Assignee: The Dow Chemical Company, Midland, Mich.

[21] Appl. No.: 794,861

[22] Filed: May 9, 1977

Related U.S. Application Data

[63] Continuation-in-part of Ser. No. 657,775, Feb. 13, 1976, abandoned.

[51] Int. Cl.$^2$ .................. C07C 69/54; C08L 67/06
[52] U.S. Cl. ........................... 252/182; 260/861; 560/122; 560/117
[58] Field of Search .............. 252/182; 260/468 L, 260/861

[56] References Cited

PUBLICATIONS

Bruson, J. Am. Chem. Soc., 64, pp. 2457–2461, (1942).
Taylor, J. Org. Chem. 6, pp. 690–695, (1941).
Borgmann, "Organic Reactions," vol. 10, pp. 179–186, 203–205, 264–266, 542–544.

*Primary Examiner*—Benjamin R. Padgett
*Assistant Examiner*—Irwin Gluck
*Attorney, Agent, or Firm*—G. R. Plotecher

[57] ABSTRACT

High yields of the title adducts are obtained from an essentially salt-free process comprising contacting at subambient temperature cyclopentadiene or a substituted cyclopentadiene with an aliphatic or an inertly-substituted aliphatic ester of an $\alpha,\beta$-ethylenically unsaturated carboxylic acid, such as methyl acrylate, in the presence of a catalytic amount of base, such as tri-n-butylmethylammonium hydroxide. A novel class of Diels-Alder adducts are readily obtained by warming these Michael adducts; polyester compositions comprising the Diels-Alder adducts demonstrate good physical properties.

29 Claims, No Drawings

MICHAEL ADDUCTS OF (SUBSTITUTED) CYCLOPENTADIENE AND ESTERS: A PROCESS THEREFOR AND DERIVATIVES THEREOF

CROSS-REFERENCE TO RELATED APPLICATION

This is a continuation-in-part of our co-pending application Ser. No. 657,775 filed Feb. 13, 1976, now abandoned.

BACKGROUND OF THE INVENTION

1. Field of the Invention

This invention relates to Michael adducts of (substituted) cyclopentadiene and aliphatic or inertly-substituted aliphatic esters of $\alpha,\beta$-ethylenically unsaturated carboxylic acids. In one aspect, this invention relates to a process for preparing these adducts. In other aspects, this invention relates to Diels-Alder adducts of these Michael adducts and to polyester compositions comprising the Diels-Alder adducts.

2. Description of the Prior Art

Taylor et al., "The Michael Condensation. VII. Activation of the Methylene Group by Carbon-Carbon Unsaturation", *J. Org. Chem.*, 6, 696 (1941) teach the Michael condensation of cyclopentadiene with both benzalacetophenone and benzal-p-bromoacetophenone. These condensations are conducted at elevated pressure and over extended reaction times and produce oxime derivatives of the desired Michael adducts in low yields. The adducts themselves were not isolated.

H. A. Bruson, "The Chemistry of Acrylonitrile. I. Cyanoethylation of Active Methylene Groups", *J. Am. Chem. Soc.*, 64, 2457 (1942) and U.S. Pat. No. 2,280,058, teaches the addition of acrylonitrile to compounds having the grouping C=C—CH—C=C in a carbocycle in the presence of benzyltrimethylammonium hydroxide. These condensations are by way of Michael addition and yield poly-cyanoethylation products. Bruson reports that attempts to replace acrylonitrile with acrylic esters were unsuccessful.

U.S. Pat. No. 3,409,659 by R. L. Pruett and S. Raines teaches a modification of Bruson's addition of acrylonitrile to cyclopentadiene. By using a 4-6 molar excess of cyclopentadiene, maintaining the temperature of the reaction mass at between $-5°$ and $0°$ C., and extending the addition and post-addition reaction periods, Pruett and Raines were able to obtain low yields (from 11 percent to a maximum of 30 percent) of mono-($\beta$-cyanoethyl)cyclopentadiene.

U.S. Pat. No. 3,524,890 by E. F. Cox teaches a base-catalyzed addition of cyclopentadiene and a vicinal epoxide to produce hydroxy-containing substituted cyclopentadienes. Cox does not teach said addition with any other electrophile.

The above teachings of Taylor et al., Bruson, Pruett and Raines, and Cox are the extent of the known, based-catalyzed additions of cyclopentadiene.

The known process for preparing the Michael adducts of (substituted) cyclopentadiene and esters, e.g., functional cyclopentadiene derivatives such as methyl cyclopentadiene propionate, is illustrated by the teaching of R. L. Schaaf and C. T. Lenk. "Ferrocenes. VII. Ferrocenes from Monofunctional Cyclopentadienes", *J. Org. Chem.*, 29, 3430 (1964). Therein, an equimolar amount of sodium cyclopentadienide in tetrahydrofuran is reacted with methyl 3-bromopropionate at $-70°$ C. to yield 45 percent of said product. This process also yields a mole of sodium bromide for each mole of alkyl halide consumed. T. Kunitomo, S. Tanimoto and R. Oda, "Synthesis of Condensation Polymers from Cyclopentadienyl-Alkane Carboxylic Esters", *Kogyo Kagaku Zasshi*, 68, 1973–6 (1965), teach a similar alkylation followed by a Diels-Alder addition of the resulting functional diene with methyl acrylate. The resulting bicyclic diester monomers were independently condensed with ethylene glycol and hexamethylenediamine to yield the respective polyester and polyamide.

SUMMARY OF THE INVENTION

According to this invention, Michael adducts of (substituted) cyclopentadiene and aliphatic or inertly-substituted aliphatic esters of $\alpha,\beta$-ethylenically unsaturated carboxylic acids are prepared by a novel, base-catalyzed Michael addition process comprising contacting at a temperature between about $-40°$ and about $25°$ C., inclusive:

(a) a 5-membered carbocycle of the formula:

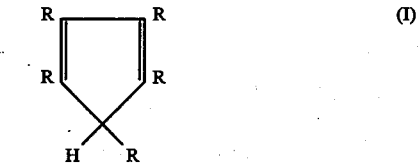

wherein each R is independently
(i) hydrocarbyl or inertly-substituted hydrocarbyl of from 1 to about 18 carbon atoms;
(ii)

wherein R' is (i) or OR" and R" is (i); or
(iii) cyano, halogen, or hydrogen with the proviso that the total carbon content, excluding the carbocycle, does not exceed about 20 carbon atoms, and with the further proviso that the total halogen and/or cyano content of the carbocycle does not exceed 3; with
(b) an aliphatic or an inertly-substituted aliphatic ester of an $\alpha,\beta$-ethylenically unsaturated carboxylic acid of 1 to about 18 carbon atoms; in the presence of
(c) a catalytic amount of base.

Since only catalytic (rather than equimolar) base is required, the process is essentially salt-free. Depending upon the choice of catalyst, the use of expensive, non-protic polar solvents or hazardous peroxide forming ether solvents can be avoided. Moreover, yields are higher, reaction times shorter, and cyclopentadiene excess lower for these additions than the known additions with acrylonitrile and benzalacetophenone.

The Michael adducts of this invention undergo Diels-Alder addition upon warming to yield a novel class of compounds. These Diels-Alder adducts are useful as polyester composition (resin) components and these compositions demonstrate good physical properties.

DETAILED DESCRIPTION OF THE INVENTION

The (substituted) cyclopentadiene here used is a 5-membered carbocycle of the formula:

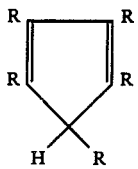

(I)

wherein each R is independently
(i) hydrocarbyl or inertly-substituted hydrocarbyl of from 1 to about 18 carbon atoms;
(ii)

wherein R' is (i) or OR" and R" is (i); or
(iii) cyano, halogen, or hydrogen with the proviso that the total carbon content, excluding the carbocycle, does not exceed about 20 carbon atoms, and with the further proviso that the total halogen and/or cyano content of the carbocycle does not exceed 3. "(Substituted) cyclopentadiene" as here used includes both unsubstituted cyclopentadiene (each R is hydrogen) and substituted cyclopentadiene (at least one R is an above-defined substituent other than hydrogen). The hydrocarbyl groups include, but are not limited to, alkyl, aryl, aralkyl, cycloalkyl and the like. By such terms as "inertly-substituted", etc., is meant that a compound of radical, e.g., hydrocarbyl, can contain substituents inert to the process reagents at the process parameters. Typical inert substituents include ester, carbonyl, amide, ether, nitrile, halogen, ethylenic unsaturation and the like. Preferably, each hydrocarbyl or inertly-substituted hydrocarbyl is of 1 to about 8 carbon atoms. The halogens of (iii) include, chlorine, bromine, and iodine. Most preferably, each R is hydrogen.

Illustrative 5-membered carbocycles include: alkyl cyclopentadienes, such as methyl-, ethyl-, propyl-, isopropyl-, pentyl-, neopentyl-, octyl-, decyl-, tetradecyl-, hexadecyl-, octadecyl-, dimethyl-, diethyl-, trimethyl-, triethyl-, tetramethyl-, tetraethyl-, pentamethyl-, pentaethyl- and pentapropyl cyclopentadienes; cycloalkyl cyclopentadienes, such as cyclopentyl-, cyclohexyl-, dicyclopentyl- and dicyclohexyl cyclopentadienes; aryl cyclopentadienes, such as phenyl-, chlorophenyl-, naphthyl- and anthracyl cyclopentadienes; aralkyl cyclopentadienes, such as benzyl-, tolyl-, phenethyl- and diphenethyl cyclopentadienes; acyl cyclopentadienes, such as benzoyl cyclopentadiene; carboxycyclopentadienes, such as the sodium, potassium and quaternary onium salts of cyclopentadienyl carboxylic acid; halogenated cyclopentadienes, such as 2-chlorocyclopentadiene, 2,4-dichlorocyclopentadiene, 2,3-dichloro-4-bromocyclopentadiene and 2,4,5-tribromocyclopentadiene; cyanocyclopentadienes, such as mono-, di- and tricyanocyclopentadienes; and the like. Of course, the 5-membered carbocycle can have any combination of the aforedescribed substituents as long as the provisoes are satisfied. Unsubstituted cyclopentadiene is the preferred reactant.

The aliphatic or inertly-substituted aliphatic esters of α,β-ethylenically unsaturated carboxylic acids (hereinafter referred to as simply esters) here used are of 1 to about 18 carbon atoms. These esters are preferably of 1 to about 12 carbon atoms and can bear inert substituents, such as aliphatic, alicyclic and aromatic hydrocarbons and others as hereinbefore defined. These inert substituents can be located on the acid and/or alcohol portions of the ester, e.g., methyl 2-entenoate, methyl 4-cyclohexyl-2-butenoate, 2-chloroethyl 2-pentenoate, etc. The alkyl esters of acrylic, methacrylic, crotonic and isocrotonic acids are representative and preferred. For example, alkyl esters include: Methyl, ethyl, propyl, isopropyl, butyl, pentyl, neopentyl, octyl and decyl acrylate, methacrylate, crotonate and isocrotonate. Unsubstituted acrylic esters are most preferred with methyl and ethyl acrylate especially preferred.

The catalytic base here used can be either added per se or generated in situ. Typical catalysts include the alkali metals, such as lithium, sodium, potassium and rubidium; alkali metal hydroxides and alkoxides, such as lithium, sodium, potassium and rubidium hydroxide; sodium and potassium methoxide and ethoxide, potassium isopropoxide, potassium t-butoxide and the like; alkali metal hydrides, such as sodium and potassium hydride, etc.; amines, such as piperazine and piperidine; trialkylamines, such as trimethylamine, triethylamine, 1,4-diazobicyclo[2.2.2]octane, bis[2-(N,N-dimethylamino)ethyl]ether, tetramethylguanidine, and the like; organo alkali metals, such as phenyl and butyl lithium and potassium naphthenide; alkali metal amides, such as sodium and potassium amide; Grignard compounds, such as ethyl magnesium chloride, propyl magnesium chloride, and the like; quaternary onium hydroxides; and suitable combinations thereof. The catalytic base can be in the form of an ion exchange resin, such as DOWEX ® MSA-1, hydroxide form (a cross-linked polystyrene resin manufactured by The Dow Chemical Company).

Quaternary onium hydroxides are the preferred catalytic bases. These bases can be either introduced per se or can be generated in situ from hydroxide and a quaternary onium salt. These salts are known in the art as phase-transfer catalysts and are described in such publications as the *J. Am. Chem. Soc.*, 93, 195 (1971) and in British Pat. No. 1,227,144 by Starks and Napier. The ammonium salts are preferred over the phosphonium salts with benzyltriethyl-, tri-n-butylmethyl-, and tetra-n-butylammonium salts most preferred. The neutralizing anion portion of the salt can be varied to convenience. Chloride, bromide and bisulfate are the preferred anions, but other representative anions include fluoride, iodide, tosylate, acetate, etc.

To further illustrate the type of quaternary onium hydroxides here used, suitable onium hydroxides are represented by the formula:

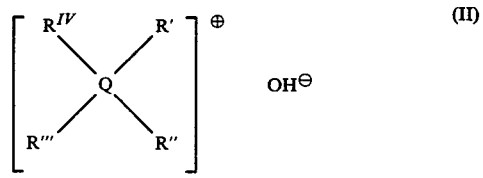

(II)

wherein:
Q is a quaternized nitrogen or phosphorus atom,
OH⊖ is a neutralizing hydroxyl anion, and
R'-R$^{IV}$ are hydrocarbyl groups of from 1 to about 16 carbon atoms each with a combined minimum total of about 10 carbon atoms.

The hydrocarbyl groups include, but are not limited to, alkyl, aryl, aralkyl, cycloalkyl, and the like. Further-more, R' can join with R", or R" with R"', etc. to form a 5- or 6-membered heterocyclic compound having at least one quaternized nitrogen or phosphorus atom in the ring and said ring may also contain one nonadjacent atom of nitrogen, oxygen or sulfur. The following compounds are illustrative: Tetrallylamonium hydroxides, such as tetra-n-butyl-, tetrahexyl-, tri-n-butylmethyl-, trioctylmethyl-, tridecylmethyl-, hexadecyltriethyl-, and hexadecyltrimethyl ammonium hydroxide; aralkyl ammonium hydroxides, such as benzyltrimethyl-, benzyltriethyl-, benzyltributyl-, and phenethyltrimethyl ammonium hydroxide; aryl ammonium hydroxides, such as N,N,N-trimethylanilinium-, N,N,N-triethylanilinium-, N,N-diethyl-N-methylanilinium-, trimethylnapthyl-, and p-methylphenyltrimethylammonium hydroxide; 5- and 6-membered heterocyclic compounds containing at least one quaternary nitrogen atom in the ring, such as N,N,N',N'-tetramethylpiperazinium dihydroxide, N,N-dimethylpiperazinium hydroxide, N-hexyl-N-ethylpiperazinium hydroxide, N,N-dibutylmorpholinium hydroxide, N,N-diethylthiazolium hydroxide, etc.; and the corresponding phosphonium hydroxides.

A catalytic amount of base is required for the practice of this invention. Of course, this amount will vary with such considerations as catalyst type, catalyst solubility, solvent, reagents, temperature, etc. Typically, the minimum amount of catalyst employed is about 0.05 mole percent based on the moles of carbocycle (cyclopentadiene or substituted cyclopentadiene) and the typical maximum amount is about 10 mole percent. The preferred minimum amount is about 0.5 mole percent with the preferred maximum amount of about 5 mole percent. Practical considerations, such as product recovery, salt formation, economics, etc., are the only reasons for the typical maximum amount of about 10 mole percent.

The controlling consideration of this invention is the competing Diels-Alder reaction. Consequently, the control (suppression) of the Diels-Alder reaction is necessary to the success (product yield) of the instant base-catalyzed Michael addition reaction. This control is best accomplished through the careful selection of various reaction parameters, such as solvent, if any, catalyst, temperature, reagent concentrations and the like. Of course, each Michael addition reaction, i.e., each combination of a (substituted) cyclopentadiene and an ester, has its own "best" reaction parameter selection.

Of the individual reaction parameters available to exert control of the Diels-Alder reaction, reaction temperature is the most influential. For purposes of this invention, the base-catalyzed Michael addition reaction proceeds at a lower temperature than the Diels-Alder reaction. Consequently, good product yields are obtained by maintaining the reaction temperature below the temperature necessary for the Diels-Alder reaction to proceed competitively.

The reaction temperature itself is dependent upon the activity of the ester but a typical minimum reaction temperature is about −40° C., preferably about −20° C., and a typical maximum reaction temperature is about 35° C., preferably about 25° C. Base-catalyzed Michael addition reactions involving the more active esters can generally be conducted at lower temperatures than similar reactions involving the less active esters. For example, methyl acrylate is more active than methyl crotonate (for purposes of this invention). Consequently, base-catalyzed Michael addition reactions between methyl acrylate and cyclopentadiene are generally conducted at a minimum temperature of about −40° C., preferably −10° C., and at a maximum temperature of about 15° C., preferably about 10° C., while similar reactions between methyl crotonate and cyclopentadiene are generally conducted at higher temperatures, i.e., a minimum temperature of about −20° C., preferably 10° C., and a maximum temperature of about 35° C., preferably about 25° C.

The base-catalyzed Michael addition reactions of this invention are exothermic and frequently require temperature control during the course of the reaction. Any suitable temperature control technique can be employed, such as a cooling apparatus, refluxing an inert, low boiling liquid or slow addition of the ester to the (substituted) cyclopentadiene.

Reaction temperature also influences the choice of catalyst to be used in the practice of this invention. For example, reduced temperatures require catalysts of good solubility, such as quaternary onium hydroxides. A solvent, such as tetrahydrofuran, can be employed at the lower temperatures (below about 0° C.) to aid in keeping the catalyst in solution. Of course, this is in turn influenced by the activity of the ester.

Pressure is not critical to this invention except as to its relationship with both the vapor pressure of the reagents, i.e., the reagents must be a liquid, and the reaction temperature. Convenience prefers ambient pressure.

The mole ratio of ester to carbocycle can vary widely depending upon the desires of the individual practitioner. The typical minimum ester:carbocycle mole ratio is about 0.05:1 and the typical maximum such mole ratio is about 10:1. If polysubstitution is desired, a large, about 5:1, mole ratio is used. If monosubstitution is desired, a mole ratio of about 0.1:1 is the preferred minimum and a mole ratio of about 0.6:1 is a preferred maximum.

Although this invention can be practiced neat, an inert, organic solvent can be used if desired. Suitable solvents are capable of dissolving the catalyst of choice and are generally employed if the catalyst is not soluble in the neat 5-membered carbocycle at reaction conditions. Typical solvents include tetrahydrofuran, methylene chloride and o-dichlorobenzene although the more polar (and expensive) solvents, such as acetonitrile, dimethyl formamide, dimethyl sulfoxide, etc., can also be used.

The Michael adducts of this invention include both isomeric, monoester substituted carbocycles, e.g., methyl cyclopentadienylpropionate (III), and polyester substituted carbocycles, e.g., dimethyl 1,3-cyclopentadienyl-1,3-dipropionate (IV).

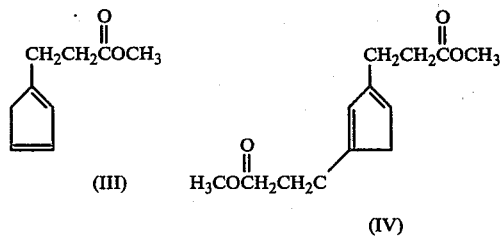

The poly-Michael adducts, i.e., carbocycles having more than one Michael-attached ester, are prepared in the same manner as mono-Michael adducts except for the difference in the ester:carbocycle mole ratio hereinbefore noted. These functional cyclopentadiene derivatives (both the mono- and poly-Michael adducts) are useful intermediates in polyester synthesis as well as in the preparation of certain specialty chemicals, such as bis-oxazolines, etc. These adducts are also useful crosslinking agents for polyolefins, polyalkylene oxides, etc. containing pendant hydroxyl or other functional groups which will react with the ester termini.

As regards polyester synthesis, a first step is to prepare Diels-Alder adducts of the Michael adducts. These former adducts constitute a novel class of compounds and are the Diels-Alder addition products of two, condensed Michael adducts. All Diels-Alder adducts of this invention comprise a (substituted) tricyclo-[5.2.1.0$^{2.6}$]-deca-3,8-diene ring structure (V) and at least two Michael-attached esters, i.e., esters attached to the ring via Michael addition.

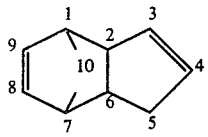

(V)

"(Substituted) tricyclodecadiene" as here used is consistent with (substituted) cyclopentadiene and includes both an unsubstituted ring and a ring substituted with the substituents and in the manner of the carbocycle (I). Since each condensed Michael adduct comprises a carbocycle having at least one Michael-attached ester, the Diels-Alder adducts have at least one such ester Michael-attached to the (substituted) tricyclodecadiene ring between the C2-C6, inclusive, positions and at least one other such ester similarly attached between the remaining (1, 7-10), inclusive, positions. Depending upon the number of Michael-attached esters and their positions on the (substituted) tricyclodecadiene ring relative to one another, a multitude of different isomers are possible. However, isomer selectively is generally not important (at least as regards polyester synthesis) and isomer mix can thus vary. Predominant isomers have an ester Michael-attached to the C-4 position and another such ester similarly attached to either the C-8 or C-9 position (assuming mono-ester substituted adducts).

The Diels-Alder adducts of this invention are prepared by warming the Michael adducts. No critical parameters are involved and warming (with or without an external heat source) to ambient (about 20°-30° C.) temperature is generally sufficient to produce a quantitative yield of dimer (although higher temperatures are preferentially employed for reasons of convenience). The Michael adducts can be either neat or solvated, pure or crude, or any combination thereof. If the Diels-Alder adducts are prepared either during Michael adduct formation or from a crude Michael addition product (comprising Michael adduct and unreacted carbocycle) other, usually undesirable, adducts are also formed. Typical "other" adducts are the Diels-Alder product of two unreacted carbocycles and the Diels-Alder product of an unreacted carbocycle and a Michael adduct. However, these other adducts are easily separated from the Diels-Alder adducts of this invention by distillation at about 190°-220° C. (whereupon all Diels-Alder adducts are cracked, i.e., create a reverse Diels-Alder reaction whereby the two condensed Michael adducts separate, and the resulting carbocycles and Michael adducts are individually recovered and subsequently recondensed). Distillation at these temperatures does not similarly cause reversion of the Michael adducts to the starting materials. This technique is particularly useful for recovering relatively pure Diels-Alder adducts from a Michael addition process conducted at or above ambient temperature.

The Diels-Alder adducts of this invention are generally hydrogenated (for reasons of thermal stability) prior to being formulated into polyester compositions. Polyester formulation temperatures typically exceed 190° C. and while these temperatures are sufficient to crack unhydrogenated Diels-Alder adducts, they are insufficient to crack hydrogenated Diels-Alder adducts. The hydrogenated adducts, i.e., tricyclodecane, include both fully hydrogenated tricyclodecadiene rings and partially hydrogenated tricyclodecadiene, i.e., tricyclodecene rings. The instant Diels-Alder adducts are hydrogenated by known hydrogenation procedures and because the C8-C9 double bond is more reactive than the C3-C4 double bond, these adducts can be selectively hydrogenated to eliminate (saturate) essentially only the C8-C9 double bond, which is required for the reverse Diels-Alder reaction, by suitable selection of catalyst and conditions. Fully hydrogenated Diels-Alder adducts are preferred.

Polyester compositions are formulated from these hydrogenated adducts in the same manner as from known diesters, such as dimethyl terephthalate. Diels-Alder adduct weight percent of the polyester composition can vary to the needs of the practitioner but compositions comprising at least about 5 weight percent are preferred. Polyester compositions comprising at least about 25 weight percent are most preferred.

The following examples are illustrative of certain specific embodiments of the invention. However, these examples are for illustrative purposes only and should not be construed as limitations upon the invention.

SPECIFIC EMBODIMENTS

EXAMPLE 1: Carbomethoxyethylation of Cyclopentadiene by Sodium Cyclopentadienide Catalyst Under a nitrogen atmosphere, freshly distilled cyclopentadiene (198 g, 3 moles) was charged to a flask equipped with a stirrer, thermometer, pressure equalizing addition funnel, condenser and nitrogen inlet and cooled in ice to about 0° C. 2.5 Molar sodium cyclopentadienide (20 ml, 0.05 mole) in tetrahydrofuran was added dropwise over ten minutes causing the temperature to rise to 8° C. The solution was cooled in an ice-methanol bath to −10° C. and an additional 20 ml of tetrahydrofuran was added to the flask. Over the next 75 minutes, methyl acrylate (86 g, 1 mole) was added to the stirred solution. The reaction temperature was controlled between about −5° and 0° C. After the methyl acrylate addition was completed, the solution was allowed to warm to about 15° C., was then washed with 100 ml of cold carbonated water, dried over calcium sulfate and the excess cyclopentadiene stripped from the cold solution under modest vacuum (50 mm). The products were separated by vacuum distillation and identified by instrumental analysis as:

| | |
|---|---|
| Methyl 3-cyclopentadienylpropionate | 62 g |
| 2:1 Methyl acrylate-cyclopentadiene adducts | 46 g |
| Higher substitution products | 9 g |
| Methyl bicyclo[2.2.1]hept-5-ene-2-carboxylate | 0.9 g |

EXAMPLE 2: Carbomethoxyethylation of Cyclopentadiene by Ion-Exchange Resin Catalyst A cross-linked polystyrene ion exchange resin (manufactured by The Dow Chemical Company under the tradename DOWEX® MSA-1, hydroxide form, 100 meq.) was stripped of excess moisture, successively equilibrated for 20 minutes with 200 ml of absolute methanol and two 200 ml volumes of tetrahydrofuran, and diluted with a final 100 ml volume of tetrahydrofuran.

Under a nitrogen atmosphere, freshly distilled cyclopentadiene (110 g, 1.66 mole) was charged to a 500 ml flask equipped with a stirrer, thermometer, pressure equalizing addition funnel with a nitrogen inlet, and a condenser connected to a glycol bubbler and then cooled to about −10° C. The DOWEX® resin was rinsed into the flask with an additional 100 ml of tetrahydrofuran. Methyl acrylate (72 g, 0.83 mole) was added over a 2 hour period with continued cooling and agitation. The DOWEX® resin was then filtered and the excess reactants were stripped from the reaction products under reduced pressure. The reaction products were vacuum distilled and determined by instrumental analysis as:

| | |
|---|---|
| Methyl 3-cyclopentadienylpropionate | 19 g |
| 2:1 Methyl acrylate-cyclopentadiene adducts | 13 g |
| Methyl bicyclo[2.2.1]hept-5-ene-2-carboxylate | 3 g |
| Methyl 3-methoxypropionate (residual methanol in ion exchange beads plus methyl acrylate) | 5 g |

EXAMPLE 3: Carbomethoxyethylation of Cyclopentadiene by Tetra-n-butylammonium Chloride/Sodium Hydroxide Catalyst in o-Dichlorobenzene To a 2-liter flask fitted with a stirrer, a thermocouple well, a condenser connected to a glycol bubbler, and a graduated pressure equalizing addition funnel was charged tetra-n-butylammonium chloride (34 g, 0.10 mole) dissolved in o-dichlorobenzene (1000 g). Freshly distilled cyclopentadiene (286 g, 4.1 mole) was then added under a nitrogen atmosphere followed by 16.1 g of 50 percent aqueous sodium hydroxide (0.20 mole) and 25 ml of distilled water. Over the next 15 minutes, a spontaneous rise in temperature, from 21° to 27° C., and the formation of the characteristic maroon color of cyclopentadienide anion (in the presence of traces of dissolved oxygen) was observed. o-Xylene (27.2 g) was added as an internal chromatographic standard and the flask contents cooled to −7° C. Methyl acrylate (351 g, 4.1 mole) was then added dropwise over 4½ hours. The principal limitation to a more rapid addition was maintaining the flask contents at a temperature of about −7° C. Unreacted methyl acrylate was not detected by vapor phase chromatography during this addition.

After the methyl acrylate addition, the flask contents were analyzed by vapor phase chromatography and found to contain:

| | | |
|---|---|---|
| Unreacted cyclopentadiene | 81 g | (70% conversion) |
| Methyl 3-cyclopentadienylpropionate | 371 g | (85% selectivity) |
| Methyl bicyclo [2.2.1]hept-5-ene-2-carboxylate | 4 g | |

The remainder of the mixture consisted of Diels-Alder and poly-Michael adducts of methyl 3-cyclopentadienylpropionate and methyl acrylate.

EXAMPLE 4: Carbomethoxyethylation of Cyclopentadiene by Tri-n-butylmethylammonium Chloride/Sodium Hydroxide Catalyst Cyclopentadiene (440 g, 6.7 mole) was charged to a 2-liter flask fitted with a stirrer, a thermocouple well, a condenser connected to a glycol bubbler, and a graduated pressure equalizing addition funnel with a nitrogen inlet. A 75 percent aqueous solution of tri-n-butylmethylammonium chloride (26.7 g, 0.085 mole) and 50 percent aqueous sodium hydroxide (13.6 g, 0.17 mole) were combined and rinsed into the flask with an additional 217 g of cyclopentadiene (3.3 mole). The flask contents were then stirred until a deep purple color developed, and then cooled to −8° C. Over the next 115 minutes methyl acrylate (147.7 g, 1.7 mole) was added, with stirring, to the cold solution (−6° to −9° C.). Upon completion of the methyl acrylate addition, the solution was stirred for an additional 60 minutes. A sample taken after this additional 60 minute period was analyzed by vapor-phase chromatography and confirmed the absence of unreacted methyl acrylate. The catalyst was then neutralized with one normal HCl (180 ml), the layers separated, and the excess cyclopentadiene distilled under reduced pressure. The product mixture was vacuum distilled at 0.5 mm to give:

| | | |
|---|---|---|
| Methyl 3-cyclopentadienylpropionate | 200 | g (80% yield based on methyl acrylate) |
| 2:1 Methyl acrylate-cyclopentadiene adducts | 16 | g |
| Methyl bicyclo[2.2.1]hept-5-ene-2-carboxylate | 4 | g |

The above examples indicate, contrary to the teaching of Bruson, that a base-catalyzed Michael addition between cyclopentadiene and methyl acrylate can be achieved in good yield without significant formation of the Diels-Alder adduct, i.e., methyl bicyclo[2.2.1]hept-5-ene-2-carboxylate.

EXAMPLE 5: Dimer Preparation

A freshly distilled sample of methyl 3-cyclopentadienylpropionate (26 g, boiling point 46°–48° C. at 0.4 torr) prepared by the procedure of Example 4 was warmed to and maintained at about 98° C. for 3 hours. The viscosity increased noticeably. Subsequent vapor phase chromatography analysis revealed essentially quantitative dimerization, i.e., Diels-Alder condensation (residual monomer content less than 4 weight percent). Dimer (Diels-Alder adduct) structure was confirmed by instrumental analysis. The olefinic region of the nuclear magnetic resonance (NMR) spectrum, integrated for about 2.2 vinyl hydrogens, indicated that the Michael-attached esters of this dimer were positioned principally at the olefin sites of the tricyclodecadiene ring. The dimer product had a boiling range of 115°–120° C. (at 0.3 torr).

EXAMPLE 6: Hydrogenation of Methyl 3-Cyclopentadienylpropionate Dimer

Because the dimer's tricyclodecadiene olefinic bonds have differing reactivities, one or both can be hydrogenated by suitable choice of catalyst and conditions.

A. The dimer (11.4 g, 37 mmole) prepared in Example 5 was dissolved in a slurry of platinum catalyst (1 g, 5 weight percent on carbon) in absolute ethanol (115 g). The slurry was then charged to a pressure bottle and pressurized with hydrogen to 30 psig on a Parr shaker hydrogenation apparatus at ambient temperature (24°-25° C.). After one mole equivalent of hydrogen had been consumed, the pressure was released, the catalyst filtered and the solvent removed by rotary evaporation under reduced pressure. A colorless oil (10.3 g) was recovered and confirmed by vapor phase chromatography as free from starting material; only one olefinic bond (1645 cm$^{-1}$) remained and the cyclopentene hydrogen was the only signal in the olefinic region of the nuclear magnetic resonance spectrum.

B. A separate portion of the dimer (15 g, 49 m mole) prepared in Example 5 was similarly hydrogenated over rhodium (3 g, 5 weight percent on carbon) in absolute ethanol (125 ml) at an initial hydrogen pressure of 55 psig. Two mole equivalents of hydrogen were readily consumed. A pale yellow concentrated product was recovered and demonstrated no evidence of residual unsaturation in either infrared or nuclear magnetic resonance spectra; the methoxyl to aliphatic hydrogen NMR integral ratio was 6:22.

EXAMPLE 7: Unsaturated, General Purpose Polyester Composition

A fully hydrogenated diester, i.e., dimer (95 g, 0.31 mole) prepared by the procedure of Example 6, propylene glycol (51.7 g, 0.68 mole) and an initiator of calcium acetate (0.06 g) and antimony oxide (0.01 g) were charged to a resin reactor equipped with a nitrogen sparge, steam condenser and stirrer. The charge was heated to about 220° C. over 4 hours whereat methanol (18 g) was discharged with the charge cooling to about 150° C. Maleic anhydride (30 g) was then charged to the reactor and the contents heated to about 200° C. over 45 minutes and subsequently held thereat for an additional 3 hours. Thereafter an acid number of 27 was determined, the reactor allowed to cool, and resin (~150 g) collected therefrom.

A mixture consisting of about 65 percent resin, 34 percent styrene monomer and 1 percent p-benzoquinone (as an inhibitor) was cast and thermally cured (50° → 120° C. over 2 hours and then held thereat for an additional 24 hours). A hard, clear, ⅛ inch thick crosslinked, unfilled, polyester composition was recovered and exhibited the following properties:

| Tensile Strength (psi) | 9,377 |
| Tensile Moldulus (psi) | 4.7 × 10⁵ |
| Flexural Strength (psi) | 14,074 |
| Flexural Modulus (psi) | 473,941 |
| Elongation (%) | 5.4 |
| Heat Distortion (° C) | 63 |
| Izod Impact (Notched ft lb/in) | 0.42 |

Although the invention has been described in considerable detail by the cyclopentadiene/methyl acrylate illustration, it must be understood that such detail was for the purpose of illustration only, and many variations and modifications can be made by one skilled in the art without departing from the spirit and scope of the invention.

What is claimed is:

1. A base-catalyzed Michael addition process for preparing Michael adducts of unsubstituted and substituted cyclopentadiene and aliphatic esters of α,β-ethylenically unsaturated carboxylic acids which can contain substituents inert to the process reagents at the process conditions, the process comprising contacting at a temperature between about −40° and about 35° C., inclusive:

(a) a 5-membered carbocycle of the formula:

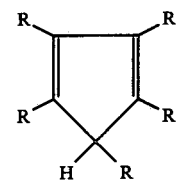

wherein each R is independently
   (i) hydrocarbyl or inertly-substituted hydrocarbyl of from 1 to about 18 carbon atoms;
   (ii)

wherein R' is (i) or OR" and R" is (i); or
   (iii) cyano, halogen, or hydrogen with the proviso that the total carbon content, excluding the carbocycle, does not exceed about 20 carbon atoms, and with the further proviso that the total halogen and/or cyano content of the carbocycle does not exceed 3; with (b) an aliphatic ester of an α,β-ethylenically unsaturated carboxylic acid of 1 to about 18 carbon atoms which can contain substituents inert to the process reagents at the process conditions; in the presence of (c) a catalytic amount of base.

2. The process of claim 1 wherein the ester and carbocycle are present at an ester:carbocycle mole ratio between about 0.05:1 and about 10:1, inclusive.

3. The process of claim 2 wherein the base is present in an amount of at least about 0.05 mole percent based upon the moles of carbocycle.

4. The process of claim 3 wherein each hydrocarby or inertly-substituted hydrocarby is of 1 to about 8 carbon atoms.

5. The process of claim 4 wherein each R is hydrogen or hydrocarbyl.

6. The process of claim 4 wherein each R is hydrogen.

7. The process of claim 6 wherein the esters are alkyl or inertly-substituted alkyl esters of acrylic, methacrylic, crotonic or isocrotonic acid.

8. The process of claim 6 wherein the ester is an alkyl or an inertly-substituted alkyl ester of acrylic acid.

9. The process of claim 8 wherein the base is dissolved in an inert, organic solvent.

10. The process of claim 9 wherein the base is a quaternary onium hyroxide.

11. The process of claim 10 wherein the base is of the formula:

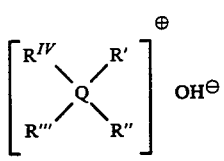

wherein:
Q is a quaternized nitrogen or phosphorus atom;
$OH^{\ominus}$ is a neutralizing hydroxyl anion, and
$R'-R^{IV}$ are hydrocarbyl groups of from 1 to about 16 carbon atoms each with a combined minimum total of about 10 carbon atoms.

12. The process of claim 11 wherein the base is benzyltriethyl-, tri-n-butylmethyl-, or tetra-n-butyl ammonium hydroxide.

13. The process of claim 12 wherein the base is present in an amount between about 0.5 and about 10 mole percent based upon the moles of carbocycle.

14. The process of claim 13 wherein the ester is methyl acrylate.

15. The process of claim 14 wherein the ester:carbocycle mole ratio is between about 0.1:1 and about 0.6:1.

16. The process of claim 15 wherein the temperature is between about −10° and about 15° C.

17. The process of claim 16 wherein the contacting is conducted at ambient pressure.

18. A Diels-Alder adduct comprising a tricyclodecadiene ring of the formula:

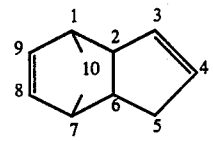

and at least two Micheal-attached aliphatic or inertly-substituted aliphatic esters of α,β-ethylenically unsaturated carboxylic acids of 1 to about 18 carbon atoms, at least one ester attached between the C2-C6, inclusive, positions and at least one other such ester attached between the remaining, inclusive, positions.

19. The adduct of claim 18 wherein the C8-C9 bond is saturated.

20. The adduct of claim 19 wherein the C3-C4 bond is saturated.

21. The adduct of claim 18 wherein the esters are alkyl or inertly-substituted alkyl esters of acrylic acid.

22. The adduct of claim 21 wherein the esters are methyl acrylate.

23. The adduct of claim 22 consisting essentially of the tricyclodecadiene ring and two Michael-attached methyl acrylate esters.

24. A composition comprising the adduct of claim 19 and a polyester.

25. A composition comprising the adduct of claim 20 and a polyester.

26. The composition of claim 25 comprising at least about 5 weight percent of the adduct.

27. The composition of claim 25 comprising at least about 25 weight percent of the adduct.

28. The composition of claim 27 wherein the adduct consists essentially of the saturated tricyclodecadiene ring and two Michael-attached methyl acrylates.

29. The composition of claim 28 comprising the adduct, maleic anhydride, propylene glycol and styrene.

* * * * *